United States Patent
Sugiyama et al.

(10) Patent No.: US 8,252,163 B2
(45) Date of Patent: Aug. 28, 2012

(54) ANALYSIS APPARATUS FOR CAPILLARY ELECTROPHORESIS

(75) Inventors: Koji Sugiyama, Kyoto (JP); Yukio Higashiisokawa, Kyoto (JP); Yusuke Nakayama, Kyoto (JP)

(73) Assignee: Arkray, Inc., Kyoto (JP)

( * ) Notice: Subject to any disclaimer, the term of this patent is extended or adjusted under 35 U.S.C. 154(b) by 491 days.

(21) Appl. No.: 12/506,940

(22) Filed: Jul. 21, 2009
(Under 37 CFR 1.47)

(65) Prior Publication Data
US 2010/0181199 A1  Jul. 22, 2010

(30) Foreign Application Priority Data

Jul. 22, 2008  (JP) ................................. 2008-188828

(51) Int. Cl.
*G01N 27/453* (2006.01)
(52) U.S. Cl. .......................... 204/603; 422/503; 356/436
(58) Field of Classification Search .......... 204/450–455, 204/600–605; 422/502–507; 356/432–444, 356/234
See application file for complete search history.

(56) References Cited

U.S. PATENT DOCUMENTS

| | | | | |
|---|---|---|---|---|
| 4,842,701 A * | 6/1989 | Smith et al. | .................... | 204/451 |
| 5,415,747 A | 5/1995 | Holloway | | |
| 5,431,793 A | 7/1995 | Wang et al. | | |
| 6,428,704 B1 | 8/2002 | Setoguchi et al. | | |
| 2002/0092770 A1 | 7/2002 | Hedberg et al. | | |
| 2003/0111348 A1 | 6/2003 | Okano et al. | | |
| 2004/0246597 A1 | 12/2004 | Ono et al. | | |
| 2009/0200166 A1 | 8/2009 | Nakayama et al. | | |
| 2010/0006436 A1 * | 1/2010 | Oishi et al. | ..................... | 204/451 |
| 2010/0051464 A1 | 3/2010 | Nakayama et al. | | |

FOREIGN PATENT DOCUMENTS

| | | |
|---|---|---|
| EP | 1114997 A2 | 7/2001 |
| EP | 1203959 A1 | 5/2002 |
| EP | 2060912 A1 | 5/2009 |
| EP | 2060913 A1 | 5/2009 |
| EP | 2144057 A1 | 1/2010 |
| JP | 7-063728 A | 3/1995 |
| JP | 2000-111539 | 4/2000 |
| JP | 2001-289820 A | 10/2001 |
| JP | 3429709 | 5/2003 |
| JP | 2003-185628 A | 7/2003 |
| JP | 2004-093297 A | 3/2004 |
| JP | 2004-361239 A | 12/2004 |
| JP | 2008-170351 | 7/2008 |
| JP | 2008-170350 | 7/2009 |
| WO | 97/12995 A1 | 4/1997 |
| WO | 2008029684 A1 | 3/2008 |
| WO | WO 2008/078781 | 7/2008 |
| WO | 2008139867 A1 | 11/2008 |

OTHER PUBLICATIONS

Extended European Search Report issued in the corresponding European Patent Application No. 09800372.6 dated Jan. 11, 2012.

\* cited by examiner

*Primary Examiner* — Jeffrey T Barton
*Assistant Examiner* — J. Christopher Ball
(74) *Attorney, Agent, or Firm* — Morgan, Lewis & Bockius LLP

(57) ABSTRACT

A capillary electrophoresis analysis apparatus is provided for analyzing samples by a capillary electrophoresis method that allows for rapid and highly accurate separation and detection.

24 Claims, 5 Drawing Sheets

ANALYSIS APPARATUS FOR CAPILLARY ELECTROPHORESIS

RELATED APPLICATIONS

This application claims the benefit of Japanese Patent Application No. 2008-188828, filed Jul. 22, 2008.

FIELD OF THE INVENTION

The present invention relates to capillary electrophoresis apparatuses for analyzing samples by capillary electrophoresis.

BACKGROUND OF THE INVENTION

Among the proteins present in blood, there are some which vary in, for example, their concentration in response to diseases, and thus can be used as indicators in the diagnosis of diseases. For example, glutamic oxalacetic transaminase (GOT) is an indicator of hepatitis, serum amylase is an indicator of pancreatitis, and the ratio of albumin to globulin is an indicator of nephrosis. These proteins in blood (blood proteins) are analyzed, for example, using cellulose acetate membrane electrophoresis methods, among others. Further, hemoglobin (Hb) which is a blood protein, includes hemoglobin A (HbA), hemoglobin F (HbF), hemoglobin S (HbS), and glycosylated hemoglobin (a glycosylated product of hemoglobin). Among these, hemoglobin S (HbS) is abnormal hemoglobin in which the $6^{th}$ glutamic acid of the $\beta$ chain is substituted with a valine. HbS is a marker in the diagnosis of sickle-cell anemia. Glycosylated hemoglobin is hemoglobin that is reacted with glucose in blood, and is used as an indicator in the diagnosis and treatment of diabetes. Glycosylated hemoglobins include hemoglobin A1a (HbA1a), hemoglobin A1b (HbA1b), hemoglobin A1c (HbA1c), and GHbLys, among others. Hemoglobin A1c is a glycosylated hemoglobin where the $\beta$-chain N-terminal valine is glycosylated. Hemoglobin A1c is an indicator that reflects previous glucose levels and is monitored as part of routine physical examinations. Because blood proteins are important indicators of various diseases, the development of apparatuses that are capable of providing rapid and accurate analysis of blood proteins are highly desired.

Examples of methods of measuring hemoglobin in blood include immunological methods, enzymatic methods, affinity chromatography methods, HPLC methods and capillary electrophoresis (CE) methods. Because immunological methods and enzymatic methods can be applied to autoanalysis apparatuses, they have the advantage of being able to handle large numbers of specimens. However, such immunological methods and enzymatic methods lack measurement accuracy. Further, regarding separation principles, affinity chromatography methods have relatively low specificity for the glycosylated valine of β-chain N-terminal, and the glycosylated lysine in a Hb molecule that is to be a component of a measured value. Therefore, the measurement accuracy for hemoglobin A1c by affinity chromatography methods is low. HPLC methods are widely used as methods of measuring hemoglobin (see, for example, JP 3429709 B). However, HPLC methods require large and expensive specialized apparatuses, and it is difficult to reduce the size and cost of these apparatuses. For applications with a number of samples, analysis apparatuses for hemoglobin would have to be reduced in size. However, as described above, it is difficult for HPLC methods to satisfy this requirement.

SUMMARY OF THE INVENTION

An aspect of the invention is a capillary electrophoresis analysis apparatus capable of rapidly and accurately analyzing a sample, such as, for example, a sample containing a blood protein, by a capillary electrophoresis method that permits for rapid and accurate analysis of the sample. The apparatus has the attributes of being of a reduced size and simplified operation, and is inexpensive to manufacture compared to other purification systems.

In an exemplary embodiment, the electrophoresis apparatus comprises an electrophoresis chip, a voltage application unit, and an absorbance measurement unit, wherein the electrophoresis chip comprises a substrate, a plurality of liquid reservoirs, and a capillary channel, wherein the plurality of liquid reservoirs are formed in the substrate, and are in communication with one another via the capillary channel, wherein the capillary channel includes a capillary channel for sample analysis, the voltage application unit comprises an electrode, and a sample to be analyzed is introduced into the capillary channel for sample analysis, wherein the capillary channel for sample analysis contains an electrophoresis running buffer, and the sample is subjected to electrophoresis by applying a voltage to the electrode, and an absorbance of the desired component(s) in the sample subjected to electrophoresis is measured by the absorbance measurement unit.

An aspect of the invention is a capillary electrophoresis analysis apparatus suitable for micro total analysis systems (μTAS).

BRIEF DESCRIPTION OF THE DRAWINGS

The following figures are simply illustrative of exemplary embodiments of the invention and are not intended to otherwise restrict the scope of the disclosure.

FIG. 1 (B) is a cross-sectional view of the electrophoresis chip shown in FIG. 1 (A) along the direction of the line I-I.

FIG. 3 (B) is a cross-sectional view of the electrophoresis chip shown in FIG. 3 (A) along the direction of the line I-I. FIG. 3 (C) is a cross-sectional view of the electrophoresis chip shown in FIG. 3 (A) along the direction of the line II-II.

FIG. 4 (B) is a perspective view of the electrophoresis chip shown in FIG. 4 (A).

DETAILED DESCRIPTION

Figure 1A:
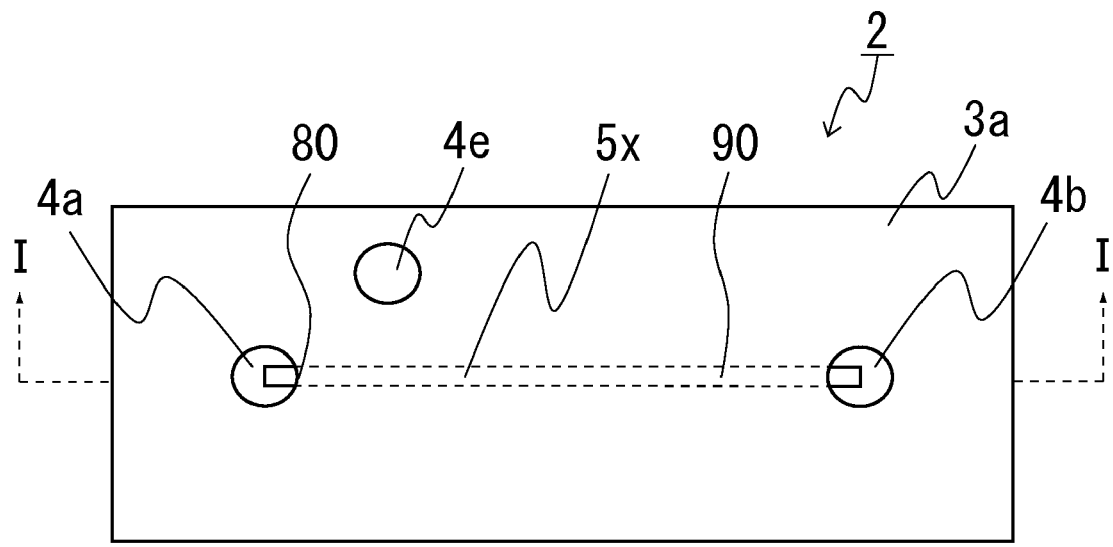
FIG. 1 (A) is a planar view of a particular embodiment of an electrophoresis chip contained in a capillary electrophoresis analysis apparatus of the invention.

In an exemplary embodiment, a capillary electrophoresis analysis apparatus of the invention comprises an electrophoresis chip, a voltage application unit, and an absorbance measurement unit, wherein the chip contains a capillary channel. The capillary electrophoresis analysis apparatus may optionally further comprise a quantitative dispensing unit, a stirring unit, a liquid sending unit, a stray light removing unit, a pre-filter component, an air-vent structure, a position adjustment unit or combinations thereof.

In an exemplary embodiment, the maximum width of the whole apparatus is in the range of about 10 cm to about 100 cm, such as about 15 cm to about 85 cm, such as about 20 cm to about 75 cm, such as about 25 cm to about 65 cm, such as about 30 cm to about 55 cm, such as about 35 cm to about 45 cm. In an exemplary embodiment, the maximum depth of the whole apparatus is in the range of about 10 cm to about 100 cm, such as about 15 cm to about 85 cm, such as about 20 cm to about 75 cm, such as about 25 cm to about 65 cm, such as about 30 cm to about 55 cm, such as about 35 cm to about 45 cm. In an exemplary embodiment, the maximum height of the whole apparatus is in the range of about 5 cm to about 100 cm, such as about 10 cm to about 85 cm, such as about 15 cm to about 75 cm, such as about 20 cm to about 65 cm, such as about 30 cm to about 55 cm, such as about 35 cm to about 45 cm.

In an exemplary embodiment, a capillary electrophoresis analysis apparatus of the invention further comprises a pre-filter component for removal of any undesired foreign materials present in the sample to be analyzed. In an exemplary embodiment, the foreign materials range in size from about 1 μm to about 5 μm. In an exemplary embodiment, the foreign materials include cell membrane fragments, plasma proteins and lipids derived from blood cells. The type and size of the filter is not limiting as long as it is able to remove the undesired materials that could potentially interfere with effective separation and analysis of a sample. In an exemplary embodiment, the filter may be derived from a metal (e.g., titanium or stainless steel), a resin (e.g., polyethylene, PEEK, polypropylene, polyethylene terphthalate, nylon, rayon, acrylic, vinylidene chloride or Teflon™), cotton, wool, coconut fiber, hemp or glass fiber. In an exemplary embodiment, use of the pre-filter component does not result in a significant increase in pressure across the filter. In an exemplary embodiment, the diameter of the filter is from about 0.1 to about 10 mm, such as about 0.5 mm to about 8 mm. In an exemplary embodiment, the thickness of the filter is from about 0.1 mm to about 5 mm, such as about 0.2 mm to about 3 mm. In an exemplary embodiment, the diameter of the filtration pore is from about 0.1 μm to about 5 μm, such as about 0.2 μm to about 3 μm. It is an objective to maintain an acceptable void ratio. The profile of the filter is not limiting as long as the filter has a structure which does not disturb the fluid flow. In exemplary embodiments, the profile is conical, columnar, circular truncated cones or two cones wherein the bottoms of the cones are in contact with each other.

In an exemplary embodiment, the value of light transmittance when the cell of the capillary electrophoresis chip is filled with buffer is higher than 50% of the light transmittance for the case where air is measured using the same light path length and absorbance measurement wavelength.

In an exemplary embodiment, a capillary electrophoresis analysis apparatus of the invention further comprises an air vent structure for venting the air that enters into the flow path of the apparatus. The positioning and size of the air vent structure is not limiting as long as air in the flow path can be effectively removed. In an exemplary embodiment, the pore diameter for air venting ranges from about 0.01 mm to about 3 mm. In an exemplary embodiment, the air vent structure contains Teflon™.

In an exemplary embodiment, a capillary electrophoresis analysis apparatus of the invention further comprises a stray light removing unit. Because the absorbance measurement accuracy is further improved by including a stray light removing unit, a more accurate measurement can be performed. In the present invention, stray light refers to light that is not contributing to detection of the transmitted light. The stray light removing unit is not particularly limited, and may include, for example an aperture, a slit or a pinhole which are arranged between the light source and the capillary channel for sample analysis. The shape of a hole of the aperture, the slit, and the pinhole is not particularly limited, and may, for example, include circular or rectangular. In exemplary embodiments where the shape of the hole of the aperture, the slit or the pinhole is circular, the diameter thereof may be in the same range as the inner diameter of the capillary channel. In exemplary embodiments where the shape of the hole of the aperture, the slit or the pinhole is rectangular, the length in the short side direction of the hole is may also be in the same range as the inner diameter of the capillary channel.

In an exemplary embodiment, a capillary electrophoresis analysis apparatus of the invention further comprises a position adjustment unit, wherein at least one of a position of the electrophoresis chip and a position of the absorbance measurement unit is capable of adjustment by the position adjustment unit.

In an exemplary embodiment, a capillary electrophoresis analysis apparatus of the invention further comprises a buffer solution and optionally a diluent.

In an exemplary embodiment, a capillary electrophoresis analysis apparatus of the invention further comprises a chip surface that has been treated with at least one of phosphoric acid, UV radiation, alkali dipping, an inorganic nanomicroparticle coating, graft co-polymerization and corona discharge as a means of suppressing undesired adsorption of a sample onto surfaces including, but not limited to, reservoir surfaces and capillary channel surfaces.

In an exemplary embodiment, a capillary electrophoresis analysis apparatus of the invention further includes a quantitative dispensing unit. Because the quantitative dispensing of a sample or reagent can be performed automatically by means of a quantitative dispensing unit, measurements can be performed with minimum effort. In an exemplary embodiment, the quantitative dispensing unit is provided in the electrophoresis chip or alternatively, outside of the electrophoresis chip.

Examples of quantitative dispensing units include, but are not limited to, a measurement channel. The measurement channel is not particularly limited and may be a part of the capillary channel of the electrophoresis chip. The measurement channel can pool or retain a certain amount of sample or reagent such as an electrophoresis running buffer. Examples of the measurement channel include, but are not limited to, a measurement channel for the sample and a measurement channel for the electrophoresis running buffer. The quantitative dispensing unit may optionally contain a suction and discharge mechanism.

In an exemplary embodiment, a capillary electrophoresis analysis apparatus of the invention further includes a stirring unit. Because a solution such as a sample, a reagent, and the like, can be mixed automatically by means of a stirring unit, a measurement can be performed simply. The stirring unit is not particularly limited and may include a stir bar. The stir bar is not particularly limited and may include a small piece of a ferromagnet whose surface is sealed with, for example, polytetrafluoroethylene. A solution in the liquid reservoir can be stirred, for example, by disposing the stir bar in a mixing liquid reservoir for mixing a sample and a reagent, and providing an electromagnetic stirring machine such as a magnetic stirrer at a bottom surface of the liquid reservoir. Alternatively, for example, the quantitative dispensing unit may serve as the quantitative dispensing unit and the stirring unit. For example, the aforementioned two solutions can be stirred by means of a quantitative dispensing unit, for example, by suction and discharging a mixture of a sample and an electrophoresis running buffer.

In an exemplary embodiment, a capillary electrophoresis analysis apparatus of the invention further include a liquid sending unit for introducing a solution (e.g., a solution containing sample) into the capillary channel. Because an electrophoresis chip can be filled automatically or introduced with a solution by means of a liquid sending unit, a measurement can be performed with minimum effort. By means of the liquid sending unit, a reagent such as an electrophoresis running buffer, an analytical reagent, a diluent, a washing liquid and a sample can be efficiently introduced into the capillary channel. The liquid sending unit is not particularly limited, and may include, for example, a suction unit, a discharge unit, and/or a voltage application unit.

In an exemplary embodiment, the suction unit (vacuum unit) is provided with a vacuum pump and a drain portion. The drain portion may, for example, be disposed at one end of the capillary channel, and the vacuum pump may be connected to the drain portion. By reducing the pressure in the capillary channel with the vacuum pump via the drain, the solution can be suctioned up and introduced into the capillary channel from the other end of the channel.

The discharge unit (pressure unit) may be provided, for example, with a pressure pump and a drain portion. The drain portion may, for example, be disposed at one end of the capillary channel and the pressure pump may be connected to the drain portion. By applying pressure to the inside of the channel by discharging air thereinto with the pressure pump via the drain, the solution can be introduced into the capillary channel by discharging air from the end of the channel.

In an exemplary embodiment, the electrophoresis chip of the capillary electrophoresis analysis apparatus comprises a substrate, a plurality of liquid reservoirs, and a capillary channel.

In an exemplary embodiment, the maximum length of the chip is in the range of about 10 mm to about 100 mm, such as about 15 mm to about 85 mm, such as about 20 mm to about 75 mm, such as about 25 mm to about 65 mm, such as about 30 mm to about 55 mm, such as about 35 mm to about 45 mm. In an exemplary embodiment, the maximum width of the chip is in the range of about 10 mm to about 60 mm, such as about 15 mm to about 55 mm, such as about 20 mm to about 50 mm, such as about 25 mm to about 45 mm, such as about 30 mm to about 40 mm. In an exemplary embodiment, the maximum thickness of the chip is in the range of about 0.3 mm to about 5 mm, such as about 0.5 mm to about 4 mm, such as about 0.7 mm to about 3 mm, such as about 1 mm to about 2 mm.

In an exemplary embodiment, the maximum length of the electrophoresis chip is the length of the portion that is longest in the longitudinal direction of the electrophoresis chip. In an exemplary embodiment, the maximum width of the electrophoresis chip is the length of the portion that is longest in the short side direction of the electrophoresis chip.

In an exemplary embodiment, the maximum thickness of the electrophoresis chip is the length of the portion that is longest along the direction (thickness direction) perpendicular to both the longitudinal direction and the short side direction of the electrophoresis chip.

In exemplary embodiments, the electrophoresis chip further comprises a blood collection mechanism or an electrophoresis chip combined with a lancet.

An electrophoresis chip of the present invention may include a single (one-piece) substrate or alternatively, more than one (i.e., multiple-piece) substrate. In an exemplary embodiment of the latter case, an electrophoresis chip of the invention comprises an upper substrate and a lower substrate, which are laminated together. The material of the substrate is not particularly limited, and examples thereof include, but are not limited to, a glass material and a polymeric material, among others. Examples of the glass material include, but are not limited to, synthetic silica glass, fused silica, and borosilicate glass. Examples of the polymeric material include, but are not limited to, cycloolefin polymer (COP), polycarbonate (PC), polydimethylsiloxane (PDMS), polystyrene (PS), polylactic acid (PLA), polyethylene (PE), polytetrafluoroethylene (PTFE), polyetheretherketone (PEEK), and an acrylic resin such as polymethylmethacrylate (PMMA).

As described herein, a suitable liquid reservoir is formed in the chip (substrate). The form is not particularly limited. In an exemplary embodiment, the liquid reservoir contains a concave (depressed) portion provided in the substrate and a space portion provided in the substrate. In an exemplary embodiment, the concave portion is formed in the thickness direction of the substrate. In an exemplary embodiment, an upper substrate and a lower substrate are provided as described herein, wherein one of the substrates, in which a through-hole is provided, may be laminated onto the other substrate. By laminating the substrate having the through-hole onto the other substrate, an opening of the through-hole is sealed at one end, and the concave portion serving as the liquid reservoir is thereby formed in the laminated body composed of both substrates. On the other hand, for example, the concave portion is formed in at least one of the substrates and both substrates may be laminated such that the surface, on which the concave portion is formed, is facing toward the other substrate. As a result of this lamination, an opening of the concave portion of one of the substrates is sealed with the other substrate, and a space serving as the liquid reservoir is thereby formed in the laminated body.

The form or design of the liquid reservoir is not particularly limited, with exemplary embodiments including, but not limited to, a quadrangular prism, a quadrangular pyramid and a cone. The form of each liquid reservoir in the substrate may all be the same or each may be different. The volume of each liquid reservoir is not particularly restricted and may be, for example, in the range of about 1 $mm^3$ to about 1000 $mm^3$, such as in the range of about 5 $mm^3$ to about 800 $mm^3$, such as about 10 $mm^3$ to about 600 $mm^3$, such as about 10 $mm^3$ to about 100 $mm^3$, such as about 20 $mm^3$ to about 500 $mm^3$, such as about 30 $mm^3$ to about 400 $mm^3$, such as about 50 $mm^3$ to about 300 $mm^3$, such as about 75 $mm^3$ to about 200 $mm^3$, such as about 85 $mm^3$ to about 150 $mm^3$ The volume of each of the liquid reservoirs may all be the same or each may be different.

The liquid reservoir is intended to define a portion of the electrophoresis apparatus where liquid can be introduced or stored. It is not required, however, that the liquid actually be introduced or stored therein. The number of liquid reservoirs is not limited. Further, a predetermined liquid reservoir may serve as more than one liquid reservoir. Examples of the liquid reservoir include, but are not limited to, a liquid reservoir for reagent, in which a reagent can be introduced or stored, a liquid reservoir for sample, in which a sample can be introduced or stored, a liquid reservoir for liquid waste, in which liquid waste is introduced or stored, and a liquid reservoir for mixing, in which the sample and the reagent are mixed. In an exemplary embodiment, the electrophoresis chip comprises a blood collection mechanism or a lancet. The liquid reservoir for sample may be in communication with the blood collection mechanism or the lancet. In this particular embodiment, the sample can be introduced into the liquid reservoir for sample from the blood collection mechanism or the lancet.

The liquid that can be introduced or stored in an electrophoresis chip of the invention may include, but is not limited to, a sample and a reagent. In an exemplary embodiment, the reagent is at least one of, for example, an electrophoresis running buffer, an analytical reagent, a diluent, and a washing liquid.

The form or design of the capillary channel is not particularly limited. In exemplary embodiments, the capillary channel may be formed in the substrate or may be a capillary tube embedded in the substrate. In the former case, for example, a groove serving as a channel is formed on the surface of the substrate. By coating an upper part of the groove with, for example, a sealing agent, the capillary channel may be formed. In another exemplary embodiment, the groove is formed in one of two substrates and the two substrates are laminated such that the surface of the substrate on which the groove is formed, faces toward the other substrate.

In an exemplary embodiment, the capillary channel for sample analysis contains a cross-sectional shape perpendicular to the channel direction. In particular embodiments, the cross-sectional shape is circular, rectangular, ellipsoidal or polygonal.

When the cross-sectional shape is circular, the diameter thereof is, in an exemplary embodiment, in the range of about 25 µm to about 100 µm, such as about 30 µm to about 80 µm, such as about 40 µm to about 70 µm, such as about 50 µm to about 65 µm.

When the cross-sectional shape is rectangular, the width thereof is, in an exemplary embodiment, in the range of about 25 µm to about 100 µm, such as about 30 µm to about 80 µm, such as about 40 µm to about 70 µm, such as about 50 µm to about 65 µm, and the depth thereof is in the range of about 25 µm to about 100 µm, such as about 30 µm to about 80 µm, such as about 40 µm to about 70 µm, such as about 50 µm to about 65 µm.

The diameter of the capillary channel is not particularly restricted, with exemplary embodiments in the range of about 1 µm to about 1000 µm, such as about 10 µm to about 800 µm, such as about 15 µm to about 650 µm, such as about 25 µm to about 500 µm, such as about 25 µm to about 100 µm, such as about 35 µm to about 400 µm, such as about 50 µm to about 300 µm, such as about 50 µm to about 200 µm. In exemplary embodiments where the cross-sectional shape perpendicular to the capillary channel direction is circular, the diameter of the capillary channel is the diameter of a circle. In select embodiments where the cross-sectional shape perpendicular to the capillary channel direction is not circular, the diameter of the capillary channel is the diameter of a circle having an area that corresponds to the cross-sectional area of a portion having the largest cross-sectional area, the dimension of the longest line that connects two points on the circumference of the cross-section.

In exemplary embodiments where the cross-sectional shape perpendicular to the capillary channel direction is rectangular, the width thereof is in the range of about 1 µm to about 1000 µm, such as about 10 µm to about 800 µm, such as about 15 µm to about 650 µm, such as about 25 µm to about 550 µm, such as about 25 µm to about 100 µm, such as about 35 µm to about 450 µm, such as about 50 µm to about 400 µm, such as about 65 µm to about 300 µm, such as about 75 µm to about 200 µm, such as about 100 µm to about 150 µm. In exemplary embodiments, the depth thereof is in the range of about 1 µm to about 1000 µm, such as about 5 µm to about 800 µm, such as about 10 µm to about 650 µm, such as about 15 µm to about 550 µm, such as about 25 µm to about 450 µm, such as about 25 µm to about 100 µm, such as about 35 µm to about 350 µm, such as about 50 nm to about 250 µm, such as about 75 nm to about 150 nm.

The length of the capillary channel is not particularly restricted and in exemplary embodiments, may be in the range of about 0.5 cm to about 15 cm, such as about 1 cm to about 10 cm such as about 2 cm to about 8 cm, such as about 3 cm to about 5 cm, such as about 1 cm to about 5 cm.

As described herein, the capillary channel includes a capillary channel for sample analysis. In an exemplary embodiment, a sample is introduced into the capillary channel for analysis, wherein the channel contains an electrophoresis running buffer. The introduced sample is then subjected to electrophoresis. Electrophoresis can be performed by creating a potential difference between both ends of the capillary channel for sample analysis with a voltage application unit as described herein. In a particular embodiment, the capillary channel for sample analysis is filled with an electrophoresis running buffer in advance or at the time of use.

In an exemplary embodiment of the capillary channel for sample analysis, the cross-sectional shape perpendicular to the capillary channel direction is circular, the diameter thereof is in the range of about 10 nm to about 200 µm, such as about 15 nm to about 150 µm, such as about 20 nm to about 100 µm, such as about 25 nm to about 85 µm, such as about 35 nm to about 75 nm. In an exemplary embodiment of the capillary channel for sample analysis, the cross-sectional shape perpendicular to the capillary channel direction is rectangular, and the width thereof is in the range of about 10 nm to about 200 µm, such as about 15 nm to about 150 µm, such as about 20 nm to about 100 µm, such as about 25 nm to about 85 µm, such as about 35 nm to about 75 nm. In an exemplary embodiment, the depth thereof is in the range of about 10 nm to about 200 nm, such as about 15 nm to about 150 µm, such as about 20 nm to about 100 µm, such as about 25 nm to about 85 µm, such as about 35 nm to about 75 nm. Providing a capillary channel for sample analysis in the aforementioned ranges makes it possible to perform accurate and rapid analyses in a capillary electrophoresis analysis apparatus of the invention. In an exemplary embodiment, the length of the capillary channel for sample analysis is in the range of about 0.5 cm to about 15 cm, such as about 1 cm to about 10 cm, such as about 2 cm to about 8 cm, such as about 3 cm to about 7 cm.

Typically, the inner walls of a glass capillary channel are negatively charged. However, the inner wall of a glass capillary channel may be coated with a positively charged coating that results in a positively charged inner wall. Further, depending on the presence or absence or types of a polar group in polymer, an inner wall of a polymeric capillary channel may be positively or negatively charged or charge-free (nonpolar). In an exemplary embodiment, a polymer that does not have a polar group may be charged by introducing a polar group.

As described herein, a capillary electrophoresis analysis apparatus of the invention includes a voltage application unit that contains electrodes. By creating a potential difference between both ends of the capillary channel for sample analysis with the voltage application unit, electrophoresis of a sample can be performed.

In an exemplary embodiment, a capillary electrophoresis analysis apparatus of the invention includes a plurality of electrodes as the voltage application unit. The electrodes may be arranged, for example, in the electrophoresis chip, such as in the liquid reservoirs. In an exemplary embodiment, through-holes that are in communication with the liquid reservoirs may be formed in the side surface of the substrate of the electrophoresis chip and electrodes may be inserted into the liquid reservoirs via these through-holes. Alternatively, cyclic electrodes may be used as the electrodes, and arranged on the wall surfaces of the liquid reservoirs on which the through-holes are provided. Disk-shaped electrodes may also be used and arranged on the bottom surfaces of the liquid reservoirs.

The material of the electrodes is not particularly limited, and may include, for example, stainless steel (SUS), platinum (Pt), and gold (Au), among others.

The voltage application unit may include an electrical wire, and a voltage generator, among others.

In an exemplary embodiment, the voltage application unit is capable of adjusting to the voltage to be applied between the electrodes. Because the voltage can suitably be set in accordance with the intended use by such voltage adjustment, the analytic accuracy of a capillary electrophoresis analysis apparatus of the invention can be further increased. In addition, due to such voltage adjustment, a capillary electrophoresis analysis apparatus of the invention can apply different voltages using the same electrodes. Therefore, the voltage application unit may further include a voltage adjustment unit such as a variable voltage generator.

In select embodiments, the voltage that is applied is not particularly limited, and may include applications for bubble detection, electrophoresis, and the like. Bubble detection is the detection of bubbles generated in the channel when a capillary channel is filled with a solution such as an electrophoresis running buffer. In an exemplary embodiment, electrophoresis is electrophoresis of a sample introduced into the capillary channel for sample analysis. In exemplary embodiments, the voltage applied for bubble detection is in the range of about 0.1 kV to about 1 kV, such as about 0.3 kV to about 0.8 kV, such as about 0.5 kV to about 0.7 kV. In exemplary embodiments, voltage applied for electrophoresis is in the range of about 0.5 kV to about 20 kV, such as about 1 kV to about 15 kV, such as about 3 kV to about 12 kV, such as about 5 kV to about 10 kV.

As described herein, a capillary electrophoresis analysis apparatus of the invention may include an absorbance measurement unit for measuring absorbance of desired components in a sample that has been subjected to electrophoresis.

In an exemplary embodiment, the absorbance of blood protein from a sample containing a blood protein can be calculated from a transmission intensity by irradiating a detection point of the capillary channel for sample analysis with light of a specific wavelength and detecting the resulting transmitted light. The absorbance measurement unit is not particularly limited, and may be composed of, for example, a light source, an optical filter, a collecting lens and a detection unit. The light source is not particularly limited, and may include, for example, a light-emitting diode (LED), and a semiconductor laser diode (LD). The optical filter is also not particularly limited, and may include, for example, a metallic interference filter or an all-dielectric interference filter. The collecting lens is not particularly limited, and may include, for example, a double-convex lens. The detection unit is not particularly limited, and may include, for example, a photodiode, a phototransistor, a photo IC and a photomultiplier tube.

A spectroscopic method of the absorbance measurement unit may include, for example, a pre-spectroscopic method and a post-spectroscopic method. In a particular embodiment, the spectroscopic method is a pre-spectroscopic method. Generally, the pre-spectroscopic method is a method in which light emitted from the light source is dispersed at a specific wavelength in advance of irradiation of a detection point. In the case of a pre-spectroscopic method, a detection point of the capillary channel for sample analysis is irradiated with the light of a specific wavelength.

As described herein, in a capillary electrophoresis analysis apparatus of the invention, the specific wavelength or range of wavelengths that are used to detect absorbance (i.e., the presence of a component of the sample) depends upon the components in the sample for which detection is desired. In an exemplary embodiment, the sample contains hemoglobin, and the desired wavelength for detection in the range of about 260 nm to about 300 nm or about 380 nm to about 450 nm, such as in the range of about 400 nm to about 430 nm.

Alternatively, the voltage application unit may be composed of, for example, an electrode, an electrical wire or a power source, or may be the aforementioned voltage application unit. Depending on the voltage application unit, a solution of a sample can be introduced into the capillary channel by applying voltage to both ends of the channel and using an electroosmotic flow thus generated.

In an exemplary embodiment, a capillary electrophoresis analysis apparatus of the invention further includes a position adjustment unit. The position adjustment unit is a unit for adjusting at least one of the position of a capillary channel for sample analysis and the position of a light flux so that the light flux of a specific wavelength can accurately be targeted at a detection point of the capillary channel for sample analysis. Because the position of the light flux with respect to the capillary channel can be adjusted by means of the position adjustment unit, the analysis accuracy of a capillary electrophoresis analysis apparatus of the present invention can be further improved.

The position adjustment unit can adjust the aforementioned position in at least one of the direction of the diameter of the capillary channel for sample analysis and the direction parallel to the channel, and preferably, the position adjustment unit can adjust the position in both the direction of the diameter of the capillary channel and the direction parallel to the channel. The position adjustment unit is not particularly limited, and may include, for example, a light source transfer unit (mechanism) or an electrophoresis chip transfer unit.

An exemplary method for adjusting a position of the light source transfer unit is as follows. First, the capillary channel for sample analysis is irradiated with a light flux while moving a light source or the like along the direction of the diameter of the capillary channel for sample analysis or the direction parallel to the channel by means of the light source transfer unit, and light scattered by the capillary channel for sample analysis is detected. When a wall of the capillary channel for sample analysis is irradiated with the light flux, the scattered light is detected as a peak value. By positioning the light source or the like at an intermediate position between two peaks, it can be adjusted so that the light flux enters the detection point at a center portion of the capillary channel for sample analysis.

The electrophoresis chip transfer unit (mechanism) can detect the scattered light and adjust the incident light on the capillary channel for sample analysis in the same manner as the light source transfer unit except that the electrophoresis chip is moved instead of the light source. Regarding the position adjustment unit, one transfer unit (mechanism) may be provided or two or more transfer units may be provided.

In an exemplary embodiment, a capillary electrophoresis analysis apparatus of the invention further includes an electrophoresis running buffer. The electrophoresis running buffer may be provided in a liquid reservoir, a capillary channel, or the like in an electrophoresis chip, or may be provided outside of the electrophoresis chip. The electrophoresis running buffer is not particularly limited, and examples thereof include a buffer solution, and the like. The buffer solution is not particularly limited, and may include, for example, morpholinoethanesulfonic acid (MES), N-(2-acetamido)iminodiacetic acid (ADA), N-(2-acetamido)-2-aminoethanesulfonic acid (ACES), N,N-bis(2-hydroxyethyl)-2-aminoethanesulfonic acid (BES), 3-morpholinopropanesulfonic acid (MOPS), N-tris(hydroxymethyl)methyl-2-aminoethanesulfonic acid (TES), and 2-[4-(2-hydroxyethyl)-1-piperazinyl]ethanesulfonic acid (HEPES).

The buffer solution may contain an acid or a weak base. Examples of the acid include, but are not limited to, maleic acid, tartaric acid, succinic acid, fumaric acid, phthalic acid, malonic acid, and malic acid. Examples of the weak base include, but are not limited to, arginine, lysine, histidine, and tris.

In an exemplary embodiment, a capillary electrophoresis analysis apparatus of the invention further includes a diluent for diluting a sample. The diluent may, for example, be provided in a liquid reservoir, in the electrophoresis chip, or may be provided outside of the electrophoresis chip. The diluent is not particularly limited, and may include, for example, distilled water, and the aforementioned buffer solution.

In an exemplary embodiment, the sample contains blood protein, wherein at least one blood protein is hemoglobin. In an exemplary embodiment, the hemoglobin is at least one of normal hemoglobin, glycosylated hemoglobin, modified hemoglobin, variant hemoglobin, and fetal hemoglobin. In an exemplary embodiment, the hemoglobin is at least one of hemoglobin A1c, hemoglobin F, hemoglobin A2, hemoglobin S, and hemoglobin C. In an exemplary embodiment, concentration of a hemoglobin is measured. In a particular embodiment, the hemoglobin is hemoglobin A1c.

In an exemplary embodiment, the sample to be analyzed is a sample of blood which is subjected to a hemolysis treatment, and the protein in the blood is hemoglobin. The blood sample is not particularly limited, and may include, for example, whole blood, blood plasma and blood serum. In a particular embodiment, whole blood is the blood sample. Examples of hemolysis treatments include, but are not limited to, a surfactant treatment, an osmotic pressure treatment, a sonication treatment, a freeze/thaw treatment, and a pressure treatment.

In an exemplary embodiment, the hemolysis treatment is at least one of a surfactant treatment, an osmotic pressure treatment, and a sonication treatment.

The surfactant treatment is not particularly limited and may, for example, be a treatment in which a blood sample is hemolyzed with a diluent to which a surfactant is added. Examples of the surfactant include, but are not limited to, saponin, and polyoxyethylene surfactant ("Triton X-100" (trade name) manufactured by Nacalai Tesque, Inc.). The osmotic pressure treatment is not particularly limited and may include a treatment in which the blood sample is hemolyzed with a solution that is adjusted to have low osmotic pressure. The solution is not particularly limited, and may include distilled water and a diluent that is adjusted to have low osmotic pressure. In a particular embodiment, the diluent is distilled water. The sonication treatment is not particularly limited and may include commonly known ultrasonic processors. The processing conditions thereof are not particularly limited.

In exemplary embodiments, the blood protein includes hemoglobin (Hb), albumin (A1b), globulin (α1, α2, β, γ globulin), fibrinogen, C-reactive protein (CRP), rheumatoid factor (RF), glutamic oxalacetic transaminase (GOT), glutamic pyruvic transaminase (GPT), creatine phosphokinase (CPK), amylase (Amy), γ-glutamyl transferase (GGT), alkaline phosphatase (ALP), fructosamine (FRA) and antistreptolysin O (ASO).

The hemoglobin is not particularly limited and may include normal hemoglobin (HbA0), glycosylated hemoglobin, modified hemoglobin, genetic variants of hemoglobin, and fetal hemoglobin (HbF). Examples of glycosylated hemoglobin include, but are not limited to, hemoglobin A1a (HbA1a), hemoglobin A1b (HbA1b), hemoglobin A1c (HbA1c), and GHbLys. Examples of hemoglobin A1c include, but are not limited to, stable HbA1c, and unstable HbA1c. Examples of modified hemoglobins include, but are not limited to, carbamoylated Hb, and acetylated Hb. Examples of variants of hemoglobin include, but are not limited to, hemoglobin S (HbS), hemoglobin C (HbC), hemoglobin M (HbM), and hemoglobin H (HbH). In exemplary embodiments, the hemoglobin is hemoglobin A1c (HbA1c), hemoglobin F (HbF), hemoglobin A2 (HbA2), hemoglobin S (HbS), or hemoglobin C (HbC). In a particular embodiment, the hemoglobin is hemoglobin A1c (HbA1c).

A capillary electrophoresis analysis apparatus of the invention may further calculate a concentration or a ratio of blood protein on the basis of the absorbance measured for the blood protein, and the analysis item may be the concentration or the ratio of a blood protein, for example. The ratio or the concentration is not particularly limited, and may include, for example, a hemoglobin concentration, an albumin concentration, a globulin concentration, a ratio of various types of hemoglobin, an albumin/glycosylated albumin ratio, an albumin/globulin ratio, and an albumin/creatinine ratio. In a particular embodiment, the hemoglobin concentration and the hemoglobin ratio are the measurements of interest. The hemoglobin concentration is not particularly limited, and may include a concentration of the aforementioned various types of hemoglobin. In an exemplary embodiment, the concentration is a hemoglobin A1c concentration, a hemoglobin F concentration, a hemoglobin A2 concentration, a hemoglobin S concentration, or a hemoglobin C concentration. In a particular embodiment, the concentration is the hemoglobin A1c concentration. The hemoglobin ratio is not particularly limited, and may include a ratio of the aforementioned various types of hemoglobin. In an exemplary embodiment, the ratio is a hemoglobin A1c ratio, a hemoglobin F ratio, a hemoglobin A2 ratio, a hemoglobin S ratio, or a hemoglobin C ratio are preferable. In a particular embodiment, the ratio is a hemoglobin A1c ratio.

In exemplary embodiments, the electroosmotic flow generated during electrophoretic separation of the components of a sample to be analyzed is in the range of about 3 to about 20 cm/min, such as about 5 to about 15 cm/min, such as about 8 to about 12 cm/min, such as about 10 to about 12 cm/min.

EXAMPLES

The examples below describe specific embodiments of a capillary electrophoresis analysis apparatus of the invention and are not intended to further restrict the scope of the invention.

Example 1

Figure 1B:
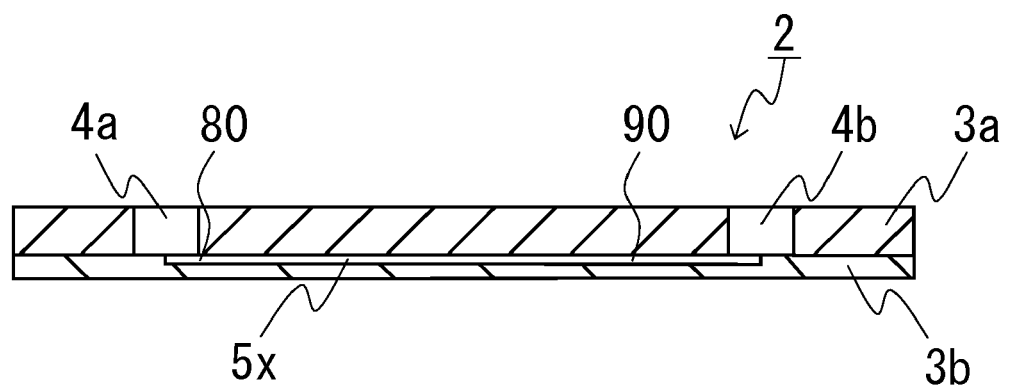

An electrophoresis chip used for the capillary electrophoresis analysis apparatus for Example 1 is shown in FIG. 1. FIG. 1 (A) is a planar view of the electrophoresis chip. FIG. 1 (B) is a cross-sectional view along the direction of line I-I of the electrophoresis chip shown in FIG. 1 (A). FIG. 1 is a schematic diagram for easier understanding. Accordingly, the size, proportions and features of each component are not intended to be limiting. As shown in FIG. 1, the electrophoresis chip 2 includes a lower substrate 3b and an upper substrate 3a, and the upper substrate 3a is laminated onto the lower substrate 3b. Three through-holes are formed in the upper substrate 3a. The bottom parts of the three through-holes of the upper substrate 3a are sealed with the lower substrate 3b by laminating the upper substrate 3a onto the lower substrate 3b, and three concave portions are formed thereby in the electrophoresis chip 2. They serve as liquid reservoirs 4a, 4b, and 4e, respectively. A groove having an "I" shape is formed on the lower substrate 3b. The upper part of the groove having an "I" shape in the lower substrate 3b is sealed with the upper substrate 3a by laminating the upper substrate 3a onto the lower substrate 3b in such a manner that this groove faces the upper substrate 3a, and a channel is formed thereby in the electrophoresis chip 2. This channel serves as a capillary channel for sample analysis 5x. The liquid reservoir 4a and the liquid reservoir 4b are in communication with each other via the capillary channel for sample analysis 5x. In contrast, the liquid reservoir 4e is not in communication with the capillary channel for sample analysis 5x and is provided as an independent liquid reservoir. An end of the capillary channel for sample analysis 5x at the liquid reservoir 4a side serves as an electrophoresis starting point 80. Further, a point on the capillary channel for sample analysis 5x between the liquid reservoir 4a and the liquid reservoir 4b serves as a detection point 90.

The electrophoresis chip 2 is a rectangular parallelepiped. However, the invention is not limited thereto. In a capillary electrophoresis analysis apparatus of the invention, the electrophoresis chip 2 may be in any form as long as it does not adversely affect the analysis of the sample. Furthermore, the electrophoresis chip 2 is composed of two substrate pieces (an upper substrate 3a and a lower substrate 3b). However, the present invention is not limited thereto. In a capillary electrophoresis analysis apparatus of the present invention, the electrophoresis chip may also be composed of a single-piece substrate.

In the electrophoresis chip 2, the length and the width of the upper substrate 3a correspond to the maximum length and the maximum width of the whole electrophoresis chip described above. Therefore, the length and the width of the upper substrate 3a are arranged to be identical to the maximum length and the maximum width of the whole electrophoresis chip described above. In the electrophoresis chip 2, the thickness of the upper substrate 3a can be designed suitably according to the volume of the liquid reservoirs 4a, 4b, and 4e, and is, for example, in the range of about 0.1 mm to about 3 mm, such as in the range of about 1 mm to about 2 mm.

In the electrophoresis chip 2, for example, the length and the width of the lower substrate 3b are the same as the length and the width of the upper substrate 3a. The thickness of the lower substrate 3b is not particularly limited, however, and may be, for example, in the range of about 0.1 mm to about 3 mm, such as about 0.1 mm to about 1 mm.

The materials comprising the upper substrate 3a and the lower substrate 3b are not particularly limited as long as they do not adversely affect the measurement of the absorbance. Examples of the materials of the upper substrate 3a and the lower substrate 3b include the aforementioned materials.

The width and the depth of the capillary channel for sample analysis 5x are not particularly limited, such that the width is, for example, in the range of about 25 µm to about 100 µm and the depth is, for example, in the range of about 25 µm to about 100 µm.

The volume of the liquid reservoirs 4a, 4b, and 4e is as described herein. In FIG. 1, the form of the liquid reservoirs 4a, 4b, and 4e is cylindrical. However, the invention is not limited thereto and the form of the liquid reservoirs 4a, 4b, and 4e may be a as described herein.

The maximum thickness of the electrophoresis chip 2 is the sum of the thickness of the upper substrate 3a and the lower substrate 3b. The respective thicknesses of the upper substrate 3a and the lower substrate 3b are as described above.

Figure 2:
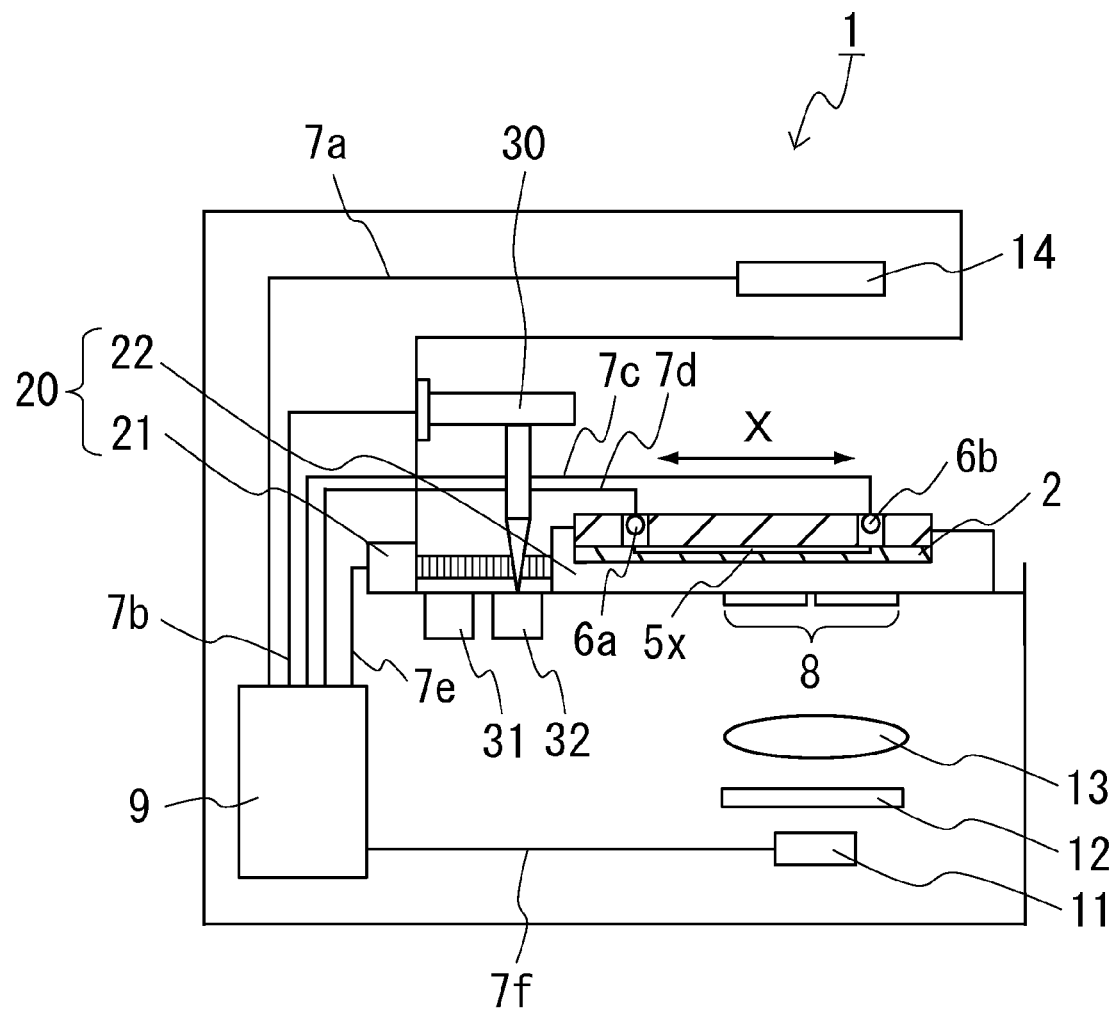
FIG. 2 is a schematic view of an exemplary embodiment of a capillary electrophoresis analysis apparatus of the invention.

A capillary electrophoresis analysis apparatus of Example 1 is shown in FIG. 2. FIG. 2 is a schematic diagram for easier understanding, and the size, proportions and like features of each component are not limited thereto and may be different therefrom. As shown in FIG. 2, this capillary electrophoresis analysis apparatus 1 includes the aforementioned electrophoresis chip 2, electrodes 6a and 6b, electrical wires 7a to 7f, a slit 8, a control unit 9, a light source 11, an optical filter 12, a collecting lens 13, a detection unit 14, an electrophoresis chip transfer unit (mechanism) 20, a quantitative dispensing unit 30, a diluent 31, and an electrophoresis running buffer 32. The electrophoresis chip transfer unit (mechanism) 20 contains a drive unit 21 and a stage 22. The electrophoresis chip 2 is arranged on the stage 22. The electrodes 6a and 6b are arranged in the liquid reservoirs 4a and 4b of the electrophoresis chip 2, respectively. The detection unit 14, the quantitative dispensing unit 30, the electrodes 6a and 6b, the electrophoresis chip transfer unit (mechanism) 20, and the light source 11 are connected to the control unit 9 via the electrical wires 7a to 7f, respectively. The control unit 9 controls power supply or the like to the aforementioned components which are connected thereto via the electrical wires 7a to 7f.

In the capillary electrophoresis analysis apparatus 1, the stage 22 is movable in a horizontal biaxial direction (an X-Y direction) by the drive unit 21 that is connected to an end thereof. The X direction and the Y direction vertically intersect on the horizontal surface. Thereby, the position of the electrophoresis chip 2 can be adjusted. Because the position of the electrophoresis chip 2 is adjusted by the electrophoresis chip transfer unit (mechanism) 20, the detection point 90 can be accurately irradiated with the light flux of a specific wavelength. Further, the quantitative dispensing unit 30 can perform a quantitative analysis of the diluent 31 and the electrophoresis running buffer 32, respectively, and can dispense them to the liquid reservoir 4a or the liquid reservoir 4e of the electrophoresis chip 2. By applying the voltage between the electrodes 6a and 6b, electrophoresis of a sample that is introduced into the capillary channel for sample analysis 5x can be performed. The light emitted from the light source 11 is dispersed at a specific wavelength by the optical filter 12 and converged by the collecting lens 13. The amount of light is increased and the stray light is removed by the slit 8, and then the sample at the detection point 90 on the capillary channel for sample analysis 5x of the electrophoresis chip 2 is irradiated. The transmitted light of the light irradiated on the detection point 90 is detected by the detection unit 14. Measurement of an absorbance of thus detected transmitted light makes it possible to analyze blood proteins contained in a sample to be analyzed.

The method of manufacturing the electrophoresis chip 2 of the capillary electrophoresis analysis apparatus 1 of Example 1 is not particularly limited and conventionally known methods can be suitably applied.

An exemplary method of analyzing blood protein using the capillary electrophoresis analysis apparatus 1 of Example 1 is described as follows:

First, the electrophoresis running buffer 32 is prepared. The electrophoresis running buffer 32, which is not particularly limited, is in a particular embodiment, a solution prepared by adding chondroitin C in a proportion of 0.8 wt % to a solution of 100 mmol/L fumaric acid and arginine acid (the solution being adjusted to pH 4.8). Next, the electrophoresis chip 2 is attached to the stage 22 and disposed in the capillary electrophoresis analysis apparatus 1. Then, a selected amount of the electrophoresis running buffer 32 is injected into the liquid reservoir 4a by the quantitative dispensing unit 30. The pressure in the capillary channel for sample analysis 5x is reduced by connecting a vacuum pump (not shown) to the liquid reservoir 4b and the capillary channel for sample analysis 5x is filled with the electrophoresis running buffer 32.

Next, the diluent 31 is injected into the liquid reservoir 4e by the quantitative dispensing unit 30. A human whole blood sample is added to the reservoir 4e and stirred by pipetting, thus generating thus a mixture of the sample and the diluent 31 is prepared. As the diluent 31, distilled water or the like can be used. Subsequently, the mixture is injected into the liquid reservoir 4a. Then, voltage is applied to the electrodes 6a and 6b, which are respectively arranged in the liquid reservoirs 4a and 4b, thereby creating a potential difference between both ends of the capillary channel for sample analysis 5x. The sample is thereby transported from the electrophoresis starting point 80 to the liquid reservoir 4b side. The voltage is not particularly limited, however is, for example, in the range of 0.5 to 20 kV.

In the same manner as described above, the light is dispersed and collected, and then the detection point 90 is irradiated with the light (at a wavelength of 415 nm), from which stray light is further removed. Then, the transmitted light at the detection point 90 is detected by the detection unit 14 and the absorbance of the blood protein in the sample is measured. An electropherogram is generated that indicates the relationship between the degree of absorbance obtained and the analysis time (from start of electrophoresis to detection).

Example 2

Figure 3A:
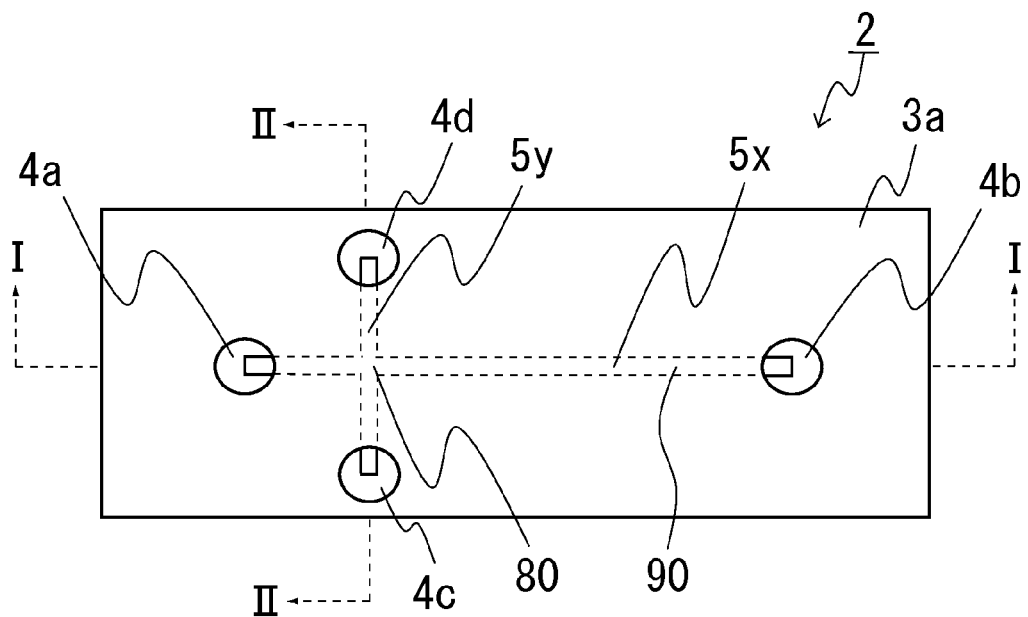
FIG. 3 (A) is a planar view of another particular embodiment of an electrophoresis chip in a capillary electrophoresis analysis apparatus of the invention.
Figure 3B:
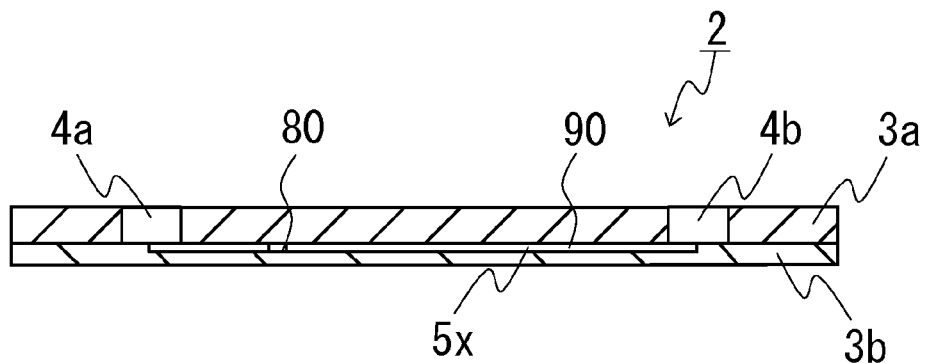
Figure 3C:
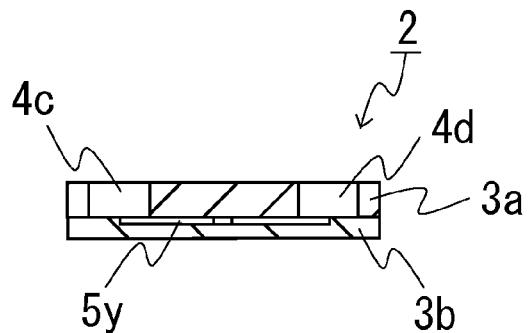

An electrophoresis chip used for the capillary electrophoresis analysis apparatus of Example 2 is shown in FIG. 3. In FIG. 3, the features that are identical to those in FIG. 1 are given the same numbers and symbols. FIG. 3 (A) is a planar view of the electrophoresis chip, FIG. 3 (B) is a cross-sectional view viewed along the direction of line I-I of the electrophoresis chip shown in FIG. 3 (A), and FIG. 3 (C) is a cross-sectional view viewed along the direction of line II-II of the electrophoresis chip shown in FIG. 3 (A). FIG. 3 is a schematic diagram for ease of understanding, but the size, proportions and like features of each component are not limited thereto.

As shown in FIG. 3, the electrophoresis chip 2 is composed of a lower substrate 3b and an upper substrate 3a, the upper substrate 3a being laminated onto the lower substrate 3b. A plurality of through-holes (four in this example) are formed in the upper substrate 3a. The bottom parts of the four through-holes formed in the upper substrate 3a are sealed with the lower substrate 3b and, four liquid reservoirs 4a to 4d are formed thereby. A cross-shaped groove is formed on the lower substrate 3b. By sealing the upper part of the cross-shaped groove formed on the lower substrate 3b with the upper substrate 3a, a capillary channel for sample analysis 5x and a capillary channel for sample introduction 5y are formed. The liquid reservoir 4a and the liquid reservoir 4b are in communication with each other via the capillary channel for sample analysis 5x. The liquid reservoir 4c and the liquid reservoir 4d are in communication with each other via the capillary channel for sample introduction 5y. The capillary channel for sample analysis 5x and the capillary channel for sample introduction 5y intersect. The capillary channel for sample analysis 5x and the capillary channel for sample introduction 5y are in communication with each other at the intersection. The intersection serves as an electrophoresis starting point 80. Further, a point on the capillary channel for sample analysis 5x between the liquid reservoir 4a and the liquid reservoir 4b serves as a detection point 90.

In the electrophoresis chip 2, the maximum length of the capillary channel for sample analysis 5x is different from that of the capillary channel for sample introduction 5y. However, the invention is not limited thereto. The maximum length of the capillary channel for sample analysis 5x may be the same as the maximum length of the capillary channel for sample introduction 5y.

The electrophoresis chip 2 has the same configuration as the electrophoresis chip shown in FIG. 1 except that the liquid reservoirs 4c and 4d and the capillary channel for sample introduction 5y are formed, and the liquid reservoir 4e is not formed. The width and the depth of the capillary channel for sample introduction 5y are the same as the width and the depth of the capillary channel for sample analysis 5x. The volume and the form of the liquid reservoirs 4c and 4d are the same as those of the electrophoresis chip shown in FIG. 1.

A capillary electrophoresis analysis apparatus 1 of Example 2 has the same configuration as the capillary electrophoresis analysis apparatus shown in FIG. 2 except that the electrophoresis chip 2 is the electrophoresis chip shown in FIG. 3 instead of the electrophoresis chip shown in FIG. 1, and electrodes 6c and 6d (not shown) are arranged in the liquid reservoirs 4c and 4d of the electrophoresis chip 2.

Next, the method of analyzing the blood protein using the capillary electrophoresis analysis apparatus 1 of Example 2 is explained.

First, the electrophoresis chip 2 is attached to a stage 22 and disposed in the capillary electrophoresis analysis apparatus 1. Subsequently, in the same manner as in Example 1, the electrophoresis running buffer 32 is injected into the liquid reservoir 4a by the quantitative dispensing unit 30. Next, in the same manner as in Example 1, the pressure in the capillary channel for sample analysis 5x is reduced by connecting a vacuum pump (not shown) to the liquid reservoir 4b, and the capillary channel for sample analysis 5x is filled with the electrophoresis running buffer 32 by the quantitative dispensing unit 30. The electrophoresis running buffer 32 is then injected into the liquid reservoir 4c. The pressure in the capillary channel for sample introduction 5y is reduced by connecting a vacuum pump (not shown) to the liquid reservoir 4d, and the capillary channel for sample introduction 5y is filled with the electrophoresis running buffer 32.

Next, the diluent 31 is injected into the liquid reservoir 4c by the quantitative dispensing unit 30. Human whole blood is added thereto as a sample and is stirred by pipetting. Voltage is applied to the electrodes 6c and 6d, thereby creating a potential difference between both ends of the capillary channel for sample introduction 5y. The sample is thereby transported to the intersection of the capillary channel for sample analysis 5x and the capillary channel for sample introduction 5y. The voltage applied between the electrodes 6c and 6d is not particularly limited, and as an example, may be in the range of about 0.5 to about 20 kV.

Voltage is applied to the electrodes 6a and 6b, thereby creating a potential difference between both ends of the capillary channel for sample analysis 5x. The sample is thereby moved from the electrophoresis starting point 80 to the liquid reservoir 4b side. The voltage is not particularly limited, and as an example, may be in the range of about 0.5 to about 20 kV.

Next, in the same manner as in Example 1, the light is dispersed and collected, and then the detection point 90 is irradiated with the light (at a wavelength of 415 nm), from which stray light is further removed. The transmitted light at the detection point 90 is detected by the detection unit 14 and the absorbance of a blood protein in the sample is measured. An electropherogram is generated that indicates the relationship between the degree of absorbance obtained and the electrophoresis time.

Example 3

Figure 4A:
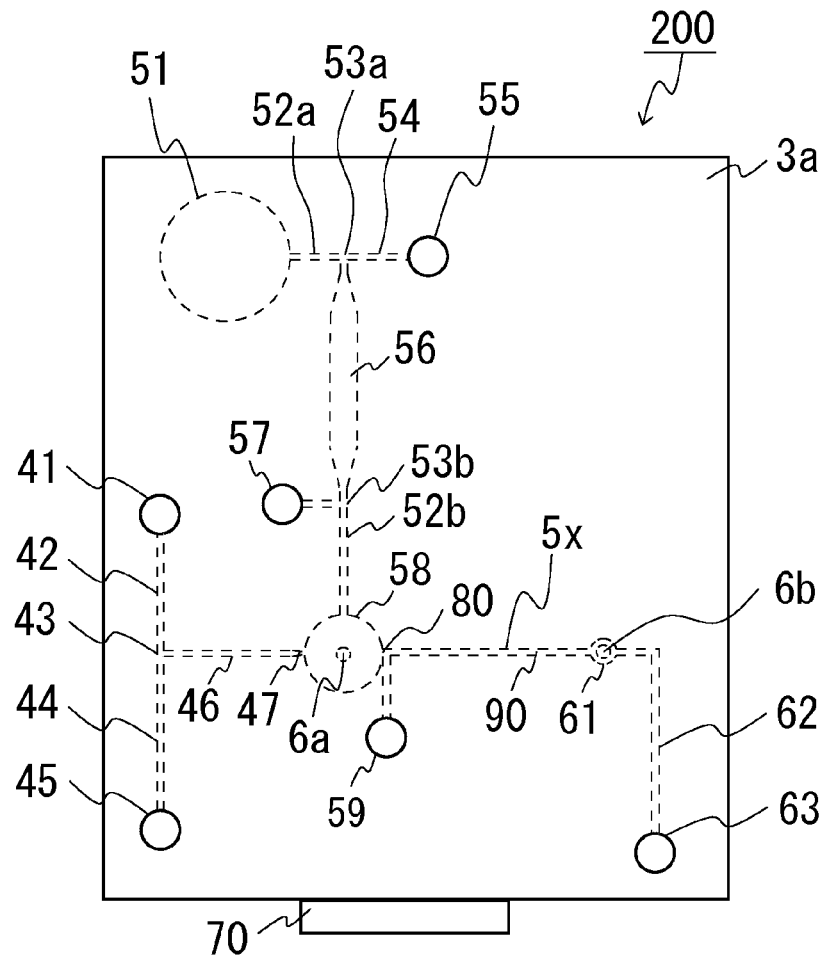
FIG. 4 (A) is a planar view of yet another particular embodiment of an electrophoresis chip in a capillary electrophoresis analysis apparatus of the invention.
Figure 4B:
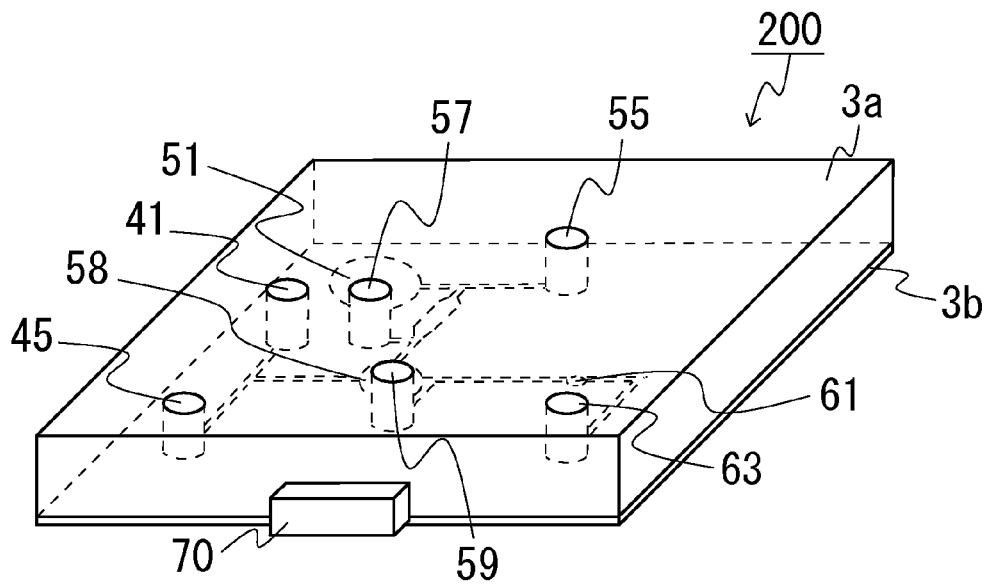

An electrophoresis chip used for the capillary electrophoresis analysis apparatus of Example 3 is shown in FIG. 4. In FIG. 4, the portions that are identical to those in FIG. 1 and FIG. 3 are given the same numbers and symbols. FIG. 4 (A) is a planar view of the electrophoresis chip, and FIG. 4 (B) is a perspective view of the electrophoresis chip. FIG. 4 is a schematic diagram for easier understanding, and the size, proportions and like features of each component are not limited thereto and may be different therefrom. As shown in FIG. 4, the electrophoresis chip 200 includes a lower substrate 3b, an upper substrate 3a, and a connector 70. The connector 70 is arranged on a side surface of a laminated body in which the upper substrate 3a is laminated onto the lower substrate 3b. A wiring pattern (not shown) is formed on the lower substrate 3b.

Six through-holes are formed in the upper substrate 3a. The bottom parts of the six through-holes are sealed with the lower substrate 3b, and six liquid reservoirs are formed thereby. The six liquid reservoirs serve as a sample introduction portion (a sample reservoir) 41, a drain 45, a drain 55, a drain 57, a drain 59, and a drain 63, respectively. Further, three concave portions of various sizes are formed at the bottom surface of the upper substrate 3a. Openings of two of the three concave portions are sealed with the lower substrate 3b, and two liquid reservoirs are formed thereby. The two liquid reservoirs serve as a reagent reservoir 51 and a diluent reservoir 58, respectively. An electrophoresis running buffer is sealed in the reagent reservoir 51. An electrode 6a connected to a wire of the wiring pattern is arranged in the diluent reservoir 58, and a stir bar (not shown) is sealed in the diluent reservoir 58. An opening of the other concave portion of the three concave portions is sealed with the lower substrate 3b, and an electrode arrangement portion 61 is formed thereby. An electrode 6b connected to a wire of the wiring pattern is arranged in the electrode arrangement portion 61. Further, a plurality of grooves is formed on the bottom surface of the upper substrate 3a. Openings of the plurality of grooves are sealed with the lower substrate 3b, and channels are formed thereby, through which the six reservoirs and the three concave portions are in communication with one another. A capillary channel, through which the diluent reservoir 58 and the electrode arrangement portion 61 are in communication with each other, serves as the capillary channel for sample analysis 5x. An end portion of the capillary channel for sample analysis 5x at the diluent reservoir 58 side serves as an electrophoresis starting point 80. Further, a point on the capillary channel for sample analysis 5x serves as a detection point 90.

Details of channels other than the capillary channel for sample analysis 5x will be described below.

The sample introduction portion 41 is in communication with the drain 45 via a sample introduction channel 42, a branching portion 43, and an overflow channel 44 in order. Further, the sample introduction portion 41 is also in communication with the diluent reservoir 58 from the branching portion 43 via a sample measurement channel 46. An opening of the sample introduction portion 41 is a sample introduction opening for introducing a sample, which contains blood protein to be analyzed, into an electrophoresis chip. At an end portion of the sample measurement channel 46 at the diluent reservoir 58 side, an orifice 47 is formed having a narrow channel cross-sectional area.

An electrophoresis chip 200 can be used to measure and introduce the sample, for example, as follows. First, after introducing a sample into the sample introduction portion 41, the sample is transported from the sample introduction portion 41 by reducing the pressure in a channel that is in communication with a vacuum pump (or the like) connected to the drain 45. Due to the suction, a sample that exceeds the volume of the sample measurement channel 46 between the branching portion 43 and the orifice 47 flows into the overflow channel 44. Subsequently, the drain 45 is closed and air is discharged with a pressure pump (not shown) that is connected to the sample introduction portion 41, with the result that and pressure is applied to the inside of a channel that is connected to the sample introduction portion 41. Thereby, a sample corresponding to the volume of the sample measurement channel 46 is introduced into the diluent reservoir 58. The introduction amount is set at the volume of the sample measurement channel 46, for example, and accordingly a sample introduction can be performed.

The reagent reservoir 51 is in communication with the drain 55 via a reagent introduction channel 52a, a branching portion 53a, and an overflow channel 54 in order. Further, the reagent reservoir 51 is also in communication with the diluent reservoir 58 from the branching portion 53a via a reagent measurement channel 56, a branching portion 53b, and a reagent introduction channel 52b. At an end portion of a channel that is branched at the branching portion 53b, the drain 57 is formed. Further, at an end portion of a channel that is branched at an end portion of the capillary channel for sample analysis 5x at the diluent reservoir 58 side, a drain 59 is formed. Furthermore, between the electrode arrangement portion 61 and the drain 63, a flow amount measurement channel 62 is formed.

For example, the electrophoresis chip 200 can have a capillary channel for sample analysis 5x filled with the electrophoresis running buffer, where the electrophoresis running buffer is introduced into the diluent reservoir 58 by measuring it as follows. First, the sample introduction portion 41, the drains 45, 55, 57, and 59 are closed, air is transported out with a vacuum pump or the like (not shown) that is connected to the drain 63, thereby reducing the pressure in channels and liquid reservoirs which are in communication with the drain 63. The reagent introduction channels 52a and 52b, the reagent measurement channel 56, the diluent reservoir 58, the capillary channel for sample analysis 5x, the electrode arrangement portion 61, and the flow amount measurement channel 62 are filled with an electrophoresis running buffer which is sealed in the reagent reservoir 51. Subsequently, the reagent reservoir 51 is closed, the drain 59 is opened, and air is removed with a vacuum pump or the like (not shown) that is connected to the drain 57, and the pressure is reduced in channels and liquid reservoirs which are in communication with the drain 57. Thereby, electrophoresis running buffer in the reagent introduction channel 52b and the diluent reservoir 58 is removed. Further, the drain 57 is closed, the drain 55 is opened, and air is suctioned out by a vacuum pump or the like (not shown) that is connected to the drain 59, and the pressure is reduced in channels and liquid reservoirs which are in communication with the drain 59. Thereby, electrophoresis running buffer corresponding to the volume of the reagent measurement channel 56 is introduced into the diluent reservoir 58. Therefore, the introduction amount is set at the volume of the reagent measurement channel 56, for example, and accordingly a measurement introduction can be performed. Further, as described above, the sample is introduced into the diluent reservoir 58. Then, the sample and the electrophoresis running buffer can be mixed by rotating the stir bar (not shown) in the diluent reservoir 58 by a magnetic stirrer (not shown). In this example, a surfactant may be added to the electrophoresis running buffer for enabling a hemolysis treatment.

In the electrophoresis chip 200, the length and the width of the upper substrate 3a are, for example, in the range of about 10 mm to about 200 mm, such as in the range of about 20 mm to about 100 mm. Further, the thickness of the upper substrate 3a is, for example, in the range of about 0.1 mm to about 10 mm, such as in the range of about 1 mm to about 5 mm.

In the electrophoresis chip 200, the length and the width of the lower substrate 3b are the same as that of the upper substrate 3a. The thickness of the lower substrate 3b is, for example, in the range of about 0.1 mm to about 10 mm.

In the electrophoresis chip 200, the material of the upper substrate 3a and the lower substrate 3b is not particularly limited as long as it does not adversely affect the measurement of the absorbance. For example, the aforementioned materials can be used as the material of the upper substrate 3a and the lower substrate 3b. Further, the lower substrate 3b is composed by laminating a plurality of substrates formed of the aforementioned materials. Between the plurality of substrates, wiring patterns made of copper foil or the like are formed.

In the electrophoresis chip 200, with respect to the diameter and the depth of the sample introduction portion 41, for example, the diameter is in the range of about 0.1 mm to about 10 mm, such as in the range of about 1 mm to about 5 mm and the depth is in the range of about 0.1 mm to about 10 mm, such as in the range of about 1 mm to about 5 mm.

In the electrophoresis chip 200, with respect to the diameter and the depth of the reagent reservoir 51, for example, the diameter is in the range of about 0.5 mm to about 50 mm, such as in the range of about 1 mm to about 20 mm and the depth is in the range of about 0.1 mm to about 10 mm, such as in the range of about 1 mm to about 5 mm.

In the electrophoresis chip 200, with respect to the diameter and the depth of the diluent reservoir 58, for example, the diameter is in the range of about 0.5 mm to about 50 mm and the depth is in the range of about 0.1 mm to about 10 mm, and preferably, the diameter is in the range of about 1 mm to about 10 mm and the depth is in the range of about 1 mm to about 5 mm.

In the electrophoresis chip 200, with respect to the diameter and the depth of the drains 45, 55, 57, 59, and 63, for example, the diameter is in the range of about 0.1 mm to about 10 mm and the depth is in the range of about 0.1 mm to about 10 mm, and preferably, the diameter is in the range of about 1 mm to about 5 mm and the depth is in the range of about 1 mm to about 5 mm.

In the electrophoresis chip 200, the form of the sample introduction portion 41, the reagent reservoir 51, the diluent reservoir 58, and the drains 45, 55, 57, 59, and 63 is cylindrical. However, the present invention is not limited thereto. In the present invention, examples of the form of each liquid reservoir include, besides a cylinder, a quadrangular prism, a quadrangular pyramid, a cone, and the like. The form of each liquid reservoir may all be the same or may each be different.

In the electrophoresis chip 200, the width and the depth of the capillary channel for sample analysis $5x$ are the same as that of the electrophoresis chip 2 shown in FIG. 1.

In the electrophoresis chip 200, with respect to the width and the depth of the reagent measurement channel 56 at the maximum portion of a cross-sectional area, for example, the width is in the range of about 0.1 mm to about 10 mm and the depth is in the range of about 0.1 mm to about 10 mm.

In the electrophoresis chip 200, with respect to the width and the depth of the orifice 47, for example, the width is in the range of about 1 μm to about 200 μm and the depth is in the range of about 1 nm to about 200 nm, and preferably, the width is in the range of about 10 nm to about 100 nm and the depth is in the range of about 10 nm to about 100 nm.

In the electrophoresis chip 200, with respect to the width and the depth of capillary channels except for the capillary channel for sample analysis $5x$, the reagent measurement channel 56, and the orifice 47, for example, the width is in the range of about 10 nm to about 1000 nm and the depth is in the range of about 10 nm to about 1000 nm, and preferably, the width is in the range of about 50 nm to about 500 nm and the depth is in the range of about 50 nm to about 500 nm.

In the electrophoresis chip 200, the maximum thickness of the whole electrophoresis chip 200 is a sum of the thickness of the upper substrate 3a and the lower substrate 3b. The thickness of the upper substrate 3a and the lower substrate 3b is as described above.

The method of manufacturing the electrophoresis chip 200 is not particularly limited and conventional methods can suitably be used, for example.

Figure 5:
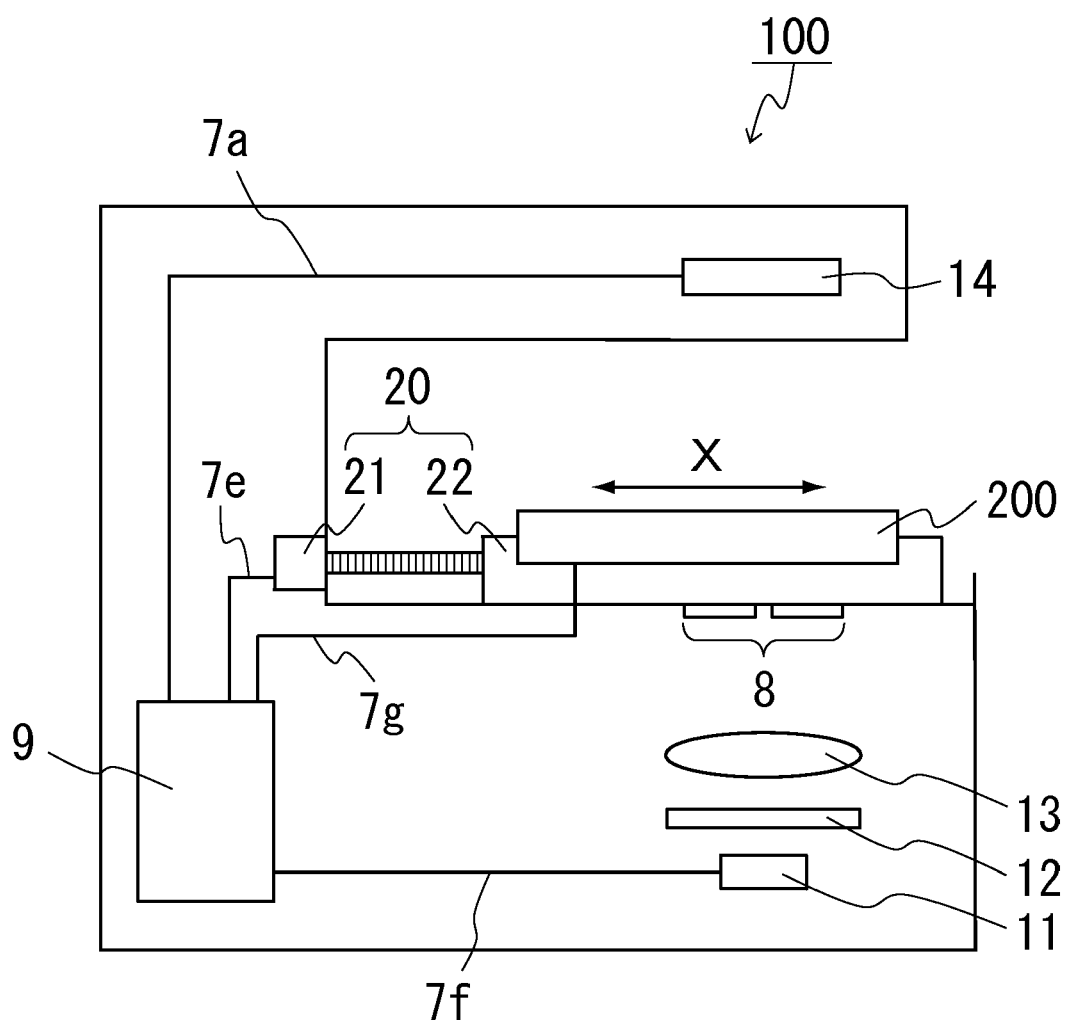
FIG. 5 is a schematic view of another exemplary embodiment of a capillary electrophoresis analysis apparatus of the invention.

A capillary electrophoresis analysis apparatus 100 of Example 3 is shown in FIG. 5. In FIG. 5, the portions that are identical to those in FIG. 2 are given the same numbers and symbols. As shown in FIG. 5, the capillary electrophoresis analysis apparatus 100 has the same configuration as the electrophoresis analysis apparatus shown in FIG. 2 except that an electrophoresis chip is the electrophoresis chip 200 shown in FIG. 4 instead of the electrophoresis chip shown in FIG. 1, the quantitative dispensing unit 30, the diluent 31, and the electrical wires 7b to 7d are not provided, and the electrophoresis running buffer is provided in the electrophoresis chip 200 and the connecting portion (not shown) of the connector 70 and an electrical wire 7g are provided. Although it is not shown in FIG. 5, the electrophoresis chip 200 is attached to the stage 22 via the connector 70 and disposed in the capillary electrophoresis analysis apparatus 100. Further, the connector 70 is connected to the control unit 9 via the electrical wire 7g. The control unit 9 controls the power supply or the like to the connector 70.

Next, a method of analyzing a blood protein using the capillary electrophoresis analysis apparatus 100 of Example 3 is explained.

First, the electrophoresis chip 200 is attached to the capillary electrophoresis analysis apparatus 100 via the connector 70. Next, as described above, the capillary channel for sample analysis $5x$ is filled with the electrophoresis running buffer. Then, as described above, the electrophoresis running buffer is measured and introduced into the diluent reservoir 58. Further, as the sample, human whole blood is introduced from the sample introduction portion 41, as described above. Human whole blood corresponding to the volume of the sample measurement channel 46 is measured and introduced into the diluent reservoir 58. The sample and the electrophoresis running buffer thus introduced are mixed in the diluent reservoir 58 and stirred by rotating the stir bar (not shown) using a magnetic stirrer (not shown).

Next, the voltage is applied to the electrodes 6a and 6b, thereby creating a potential difference between both ends of the capillary channel for sample analysis 5x. The sample is thereby moved from the electrophoresis starting point 80 to the electrode 6b side. The voltage application is performed by supplying power from the connector 70 to the electrodes 6a and 6b via the electrical wire 7g. The voltage is not particularly limited and may, for example, be in the range of about 0.5 to about 20 kV.

Next, in the same manner as in Example 1, the light is dispersed and collected, and then the detection point 90 is irradiated with the light (at a wavelength of 415 nm), from which stray light is further removed. The transmitted light at the detection point 90 is then detected by the detection unit 14 and the absorbance of a blood protein in the sample that is subjected to electrophoresis is measured. An electropherogram is generated that indicates the relationship between the degree of the absorbance obtained and the analysis time.

A capillary electrophoresis analysis apparatus of the invention enables the whole apparatus to be miniaturized, simple to operate and inexpensive to manufacture, resulting in rapid and highly accurate analyses of various samples. A capillary electrophoresis analysis apparatus of the invention is suitable for micro total analysis systems (μTAS) and is especially applicable to all technical fields where blood proteins are analyzed, such as laboratory tests, biochemical examinations and medical research.

It should be understood that the foregoing discussions and examples merely present a detailed description of certain exemplary embodiments. It should therefore be apparent to those of ordinary skill in the art that modifications and equivalents can be made without departing from the spirit and scope of the invention. All journal articles, other references, patents and patent applications that are identified in this application are incorporated by reference in their entireties.

What is claimed is:

1. A capillary electrophoresis apparatus, comprising
   an electrophoresis chip comprising
      a substrate;
      a capillary channel; and
      a plurality of liquid reservoirs in communication with each other via the capillary channel, wherein the volume of the liquid reservoirs is from about 10 mm$^3$ to about 100 mm$^3$;
   a voltage application unit comprising an electrode in communication with the capillary channel;
   an absorbance measurement unit;
   a pre-filter component;
   an air vent structure;
   a stray light removing unit; and
   a position adjustment unit,
   wherein the apparatus is capable of electrophoretic separation and detection of a sample introduced into the capillary channel wherein the detection is measured by the absorbance measurement unit;
   wherein the sample comprises hemoglobin that is at least one of hemoglobin A1c, hemoglobin F, hemoglobin A2, hemoglobin S, and hemoglobin C; and
   wherein the electrophoresis chip surface has been treated with at least one of phosphoric acid, UV radiation, alkali dipping, an inorganic nanomicroparticle coating, graft co-polymerization and corona discharge to minimize adsorption of the sample.

2. The apparatus according to claim 1, wherein the apparatus is capable of electrophoretic separation and detection of a sample introduced into the capillary channel.

3. The apparatus according to claim 1, wherein the apparatus has a width of about 10 cm to about 100 cm, a depth of about 10 cm to about 100 cm and a height of about 5 cm to about 100 cm.

4. The apparatus according claim 1, wherein the capillary channel is formed on the surface of the substrate or is a tube embedded in the substrate.

5. The apparatus according claim 1, wherein the plurality of liquid reservoirs are depressions formed on the surface of the substrate.

6. The apparatus according claim 1, wherein the electrophoresis chip has a length of about 10 mm to about 100 mm, a width of about 10 mm to about 60 mm and a thickness of about 0.3 mm to about 5 mm.

7. The apparatus according claim 1, wherein the capillary channel has a diameter of about 25 μm to about 100 μm and a length of about 0.5 cm to about 15 cm.

8. The apparatus according to claim 1, wherein the capillary channel contains a cross-sectional shape perpendicular to the channel direction.

9. The apparatus according to claim 8, wherein the cross-sectional shape is circular, rectangular, ellipsoidal or polygonal.

10. The apparatus according to claim 9, wherein when the cross-sectional shape is circular, the diameter thereof is about 25 μm to about 100 μm.

11. The apparatus according to claim 9, wherein when the cross-sectional shape is rectangular, the width thereof is about 25 μm to about 100 μm and the depth thereof is about 25 μm to about 100 μm.

12. The apparatus according to claim 1, wherein the capillary electrophoresis apparatus further comprises a quantitative dispensing unit, a stirring unit, a liquid sending unit and combinations thereof.

13. The apparatus according to claim 1, wherein the capillary channel is coated on its inner walls with a cationic, anionic or neutral coating.

14. The apparatus according to claim 1, wherein the substrate comprises an upper substrate and a lower substrate which are laminated together.

15. The apparatus according to claim 1, wherein the substrate is selected from the group consisting of a synthetic silica glass, fused silica, borosilicate glass, cycloolefin polymer (COP), polycarbonate (PC), polydimethylsiloxane (PDMS), polystyrene (PS), polylactic acid (PLA), polyethylene (PE), polytetrafluoroethylene (PTFE), polyetheretherketone (PEEK), and an acrylic resin.

16. The apparatus according to claim 1, wherein the capillary tube contains a buffer solution.

17. The apparatus according to claim 1, wherein the hemoglobin is at least one of normal hemoglobin, glycosylated hemoglobin, modified hemoglobin, variant hemoglobin, and fetal hemoglobin.

18. The apparatus according to claim 1, wherein the hemoglobin is A1c.

19. The apparatus according to claim 1, wherein a concentration of the hemoglobin is detected by the absorbance measurement unit.

20. The apparatus according to claim 19, wherein the absorbance measurement unit measures absorbance by the hemoglobin at a wavelength range of about 260 nm to about 300 nm or at a range of about 380 nm to about 450 nm.

21. The apparatus according to claim 20, wherein the wavelength range is about 400 nm to about 430 nm.

22. The apparatus according to claim 1, wherein the sample is subjected to a hemolysis treatment.

23. The apparatus according to claim 22, wherein the hemolysis treatment is at least one of a surfactant treatment, an osmotic pressure treatment, and a sonication treatment.

24. The apparatus according to claim 1, wherein the electroosmotic flow generated during electrophoretic separation of the sample is in the range of about 3 to about 20 cm/min.

* * * * *